US007697766B2

(12) United States Patent
Hammoud et al.

(10) Patent No.: US 7,697,766 B2
(45) Date of Patent: Apr. 13, 2010

(54) SYSTEM AND METHOD TO DETERMINE AWARENESS

(75) Inventors: Riad I. Hammoud, Kokomo, IN (US); Andrew L. Wilhelm, Kokomo, VA (US); Harry Zhang, Carmel, IN (US); Gerald J. Witt, Carmel, IN (US)

(73) Assignee: Delphi Technologies, Inc., Troy, MI (US)

( * ) Notice: Subject to any disclaimer, the term of this patent is extended or adjusted under 35 U.S.C. 154(b) by 1104 days.

(21) Appl. No.: 11/082,608

(22) Filed: Mar. 17, 2005

(65) Prior Publication Data

US 2006/0251297 A1 Nov. 9, 2006

(51) Int. Cl.
*G06K 9/62* (2006.01)

(52) U.S. Cl. ...................................................... 382/225

(58) Field of Classification Search ................. 382/225; 725/10; 708/542, 170, 205, 495; 712/222
See application file for complete search history.

(56) References Cited

U.S. PATENT DOCUMENTS

| | | | | |
|---|---|---|---|---|
| 5,826,224 | A * | 10/1998 | Gerson et al. | 704/222 |
| 5,859,921 | A | 1/1999 | Suzuki | |
| 6,134,270 | A * | 10/2000 | Mou | 375/240.21 |
| 6,671,391 | B1 * | 12/2003 | Zhang et al. | 382/118 |
| 6,964,023 | B2 * | 11/2005 | Maes et al. | 715/811 |
| 2003/0227539 | A1 * | 12/2003 | Bonnery et al. | 348/14.1 |
| 2004/0066853 | A1 * | 4/2004 | Chen et al. | 375/240.27 |
| 2004/0179719 | A1 * | 9/2004 | Chen et al. | 382/118 |

FOREIGN PATENT DOCUMENTS

| | | |
|---|---|---|
| DE | 10051228 | 10/2002 |
| EP | 1 386 786 | 2/2004 |
| WO | WO 0269266 | 6/2002 |

OTHER PUBLICATIONS

Said et al. (A New, Fast, and Efficient Image Codec Based on Set of Partitioning in Hierarchical Trees, Jun. 1996, IEEE Transactions on Circuits and Systems for Video Technology, vol. 6, No. 3, pp. 243-250.*

Kisacanin et al., Real-Time Vision for Human-Computer Interaction: Real-Time Algorithms: From Signal Processing to Computer Vision, 2005, Spinger US,pp. 15-40.*

European Patent Office Communication for Application No. 06075527.9-2215, dated Sep. 17, 2007, 14 pages.

EP Search Report dated Jul. 14, 2006.

Smith P etal: "Monitoring head/eye motion for driver alertness with one camera" Pattern Recognition, 2000. Proceedings. 15th International Conference on Sep. 3-7, 2000, Los Alamitos, CA, USA, IEEE Comput. Soc, US, vol. 4, Sep. 3, 2000, pp. 636-642, XP010533160 ISBN: 0-7695-0750-6 p. 636, right-hand column, paragraph 4-p. 636, right-hand column, last line p. 638, right-hand column, last paragraph p. 639, left-hand column, paragraph 1 p. 641, left-hand column, last paragraph; figures 1-13.

(Continued)

*Primary Examiner*—Bhavesh M Mehta
*Assistant Examiner*—Dennis Rosario
(74) *Attorney, Agent, or Firm*—Jimmy L. Funke

(57) ABSTRACT

A system for measuring the awareness of a subject including an imaging device adapted to acquire data representative of an image of the subject, and an awareness processor connected to the imaging device, wherein the awareness processor is adapted to classify the awareness of the subject according to the position of the subject.

21 Claims, 8 Drawing Sheets

100
102
Digitizer
114
104
Pre-Processing Section
106
110
Warning Device
Classifying Section
108

OTHER PUBLICATIONS

EP Search Report dated Jan. 12, 2007.

Database Inspec [Online] The Institution of Electrical Engineers, Stevenage, GB; Dec. 4, 2003, Smith P et al: "Determining driver visual attention with one camera" XP002404338 Database accession No. 7886420 abstract -& IEEE Transactions on Intelligent Transportation System IEEE USA, vol. 4 No. 4, Dec. 4, 2003; pp. 205-218, XP002411909 ISSN: 1524-9050.

Database WPI Week 200272 Derwent Publications Ltd., London, GB; AN 2002-675082 XP002404344 -& WO 02/069266 A1 (SETP One Co Ltd) Sep. 6, 2002 abstract.

Zhao Jiali et al: "Face recognition: a facial action reconstruction and ICA representation approach" Info-Tech and Info-Net, 2001. Proceedings. ICII 2001—Bejing. 2001 International Conferences on Oct. 29-Nov. 1, 2001, Piscataway, NJ, USA, IEEE, vol. 3, Oct. 29, 2001, ISBN:0-7803-7010-4 p. 459-p. 460.

Spors S et al: "A real-time face tracker for color video" 2001 IEEE International Conference on Accoustics, Speech, and Signal Processing. Proceedings. (ICASSP). Salt Lake City, UT, May 7-11, 2001, IEEE International Conference on Acoustics, Speech, and Signal Processing (ICASSP), New York, NY: IEEE, US, vol. vol. 1 of 6, May 7, 2001, pp. 1493-1496, XP010802917 ISBN: 0-7803-7041-4 p. 1494, right-hand column, paragraph 2.4—p. 1494, last line.

Acosta E et al: "An automatic face detection and recognition system for video indexing applications" 2002 IEEE International Conference on Acoustics, Speech, and Signal Processing. Proceedings. (ICASSP). Orlando, FL, May 13-17, 2002, IEEE International Conference on Accoustics, Speech, and Signal Processing (ICASSP), New York, NY:IEEE, US, vol. vol. 4 of 4, May 13, 2002, pp. IV-3644, XP 010804390 ISBN: 0-7803-7402-9 p. 3646.

* cited by examiner

SYSTEM AND METHOD TO DETERMINE AWARENESS

TECHNICAL FIELD

The present invention generally relates to detecting the positional state of an object, and in particular to a system and method for approximating operator awareness based on the positional state of one or more operator features.

BACKGROUND

A primary task when operating a vehicle, such as, driving an automobile, flying a plane, conducting a train or the like, is to monitor vehicular movement to ensure safe passage of the vehicle and its contents. Often times, however, a vehicle operator will become distracted. Some common distractions include fatigue, talking on or dialing a phone, interacting with passengers, reading road signs, or the like. Such distractions tend to direct the attention of the operator away from this primary task, and contribute to many, possibly avoidable, accidents. Human factors research, moreover, shows that a distracted driver reacts slower to unpredictable and potentially dangerous events, each of which might be avoided provided increased operator awareness.

To address these and additional issues previous systems have been proposed wherein devices periodically or randomly require an operator to manually respond to an awareness indicator by pressing a button, or the like. If a response is not received, the device generates an alarm alerting the operator of potential danger. Other proposed devices attempt to monitor driver awareness based on heart metrics. For example, the device may measure fluctuations in heart rate, blood pressure, or irregular heart beat patterns. While these attempts, allegedly, increase driver awareness during times of fatigue, they are crude measures that are susceptible to false signals.

SUMMARY

To solve these and other problems associated with conventional devices that measure operator awareness, the inventors have developed a system for measuring the awareness of a subject including an imaging device adapted to acquire data representative of an image of the subject, and an awareness processor connected to the imaging device, wherein the awareness processor is adapted to classify the awareness of the subject according to the position of the subject.

A method of the invention comprises the steps of acquiring data representative of an image of a subject, and processing the data. The processing step includes identifying a particular region of the image data, normalizing the data in the particular region to a pre-defined size; and determining subject awareness based on the orientation of a portion of the subject represented by the normalized data in said particular region.

DETAILED DESCRIPTION

Figure 1:
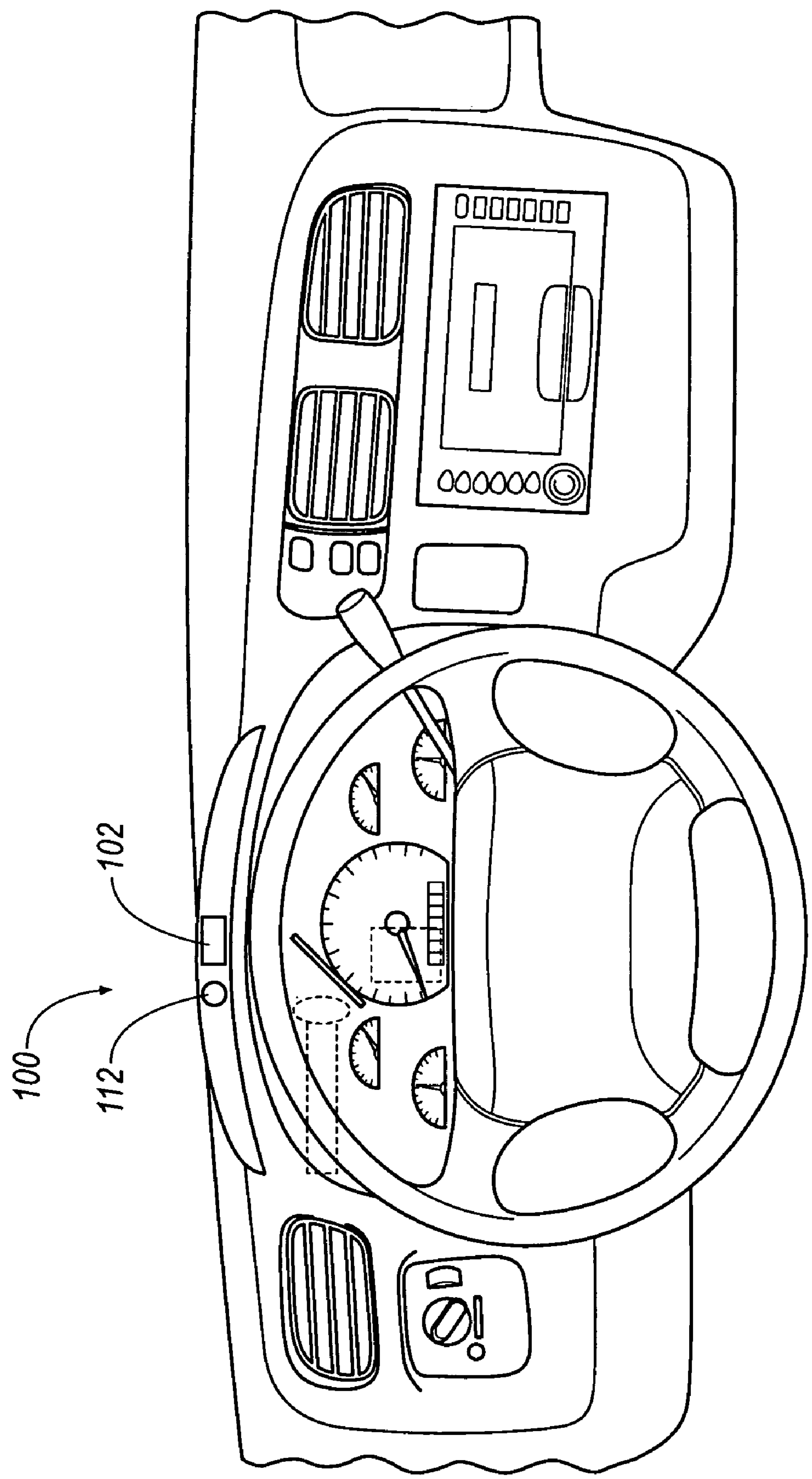
FIG. 1 is a perspective showing an embodiment of the present invention.

Referring now to the drawings, wherein like numbers represent like elements, a visual awareness detection system 100 installed in a vehicle is generally shown according to an embodiment of the present invention in FIG. 1. An image acquisition device 102 is shown generally directed at the facial region of an operator.

For purposes of convenience, the image acquisition device 102 will be referred to as a camera that is coordinated to measure luminescence provided from an infrared illuminator. It should be noted, however, that the present invention can be practiced with any type of image acquisition device and any type of illumination device. Thus, for example, devices and systems that provide and detect any type of energy (e.g. light, heat, or the like) could equally be implemented to acquire or create an analogous image. One of ordinary skill in the art will recognize these and other various ways to acquire the desired image to be processed by the visual awareness processor 104. Traditionally, three-dimensional images have yielded higher levels of detail, and, therefore, multiple camera configurations have often been implemented for various facial analyses. Although a plurality of cameras 102 may be used to practice the invention, the illustrated embodiments of the present invention as generally seen in FIG. 1, employs a single camera 102.

The camera 102 is situated to capture one or more images of an object in the vehicle, and specifically the facial region of an operator. The camera 102 may be located in any desired position within the vehicle to adequately capture the image of the object. For example, the camera 102 may be housed within a dashboard as seen in FIG. 1. In another example, the camera 102 maybe housed in a rear-view mirror, in a roof, or the like.

Figure 2:
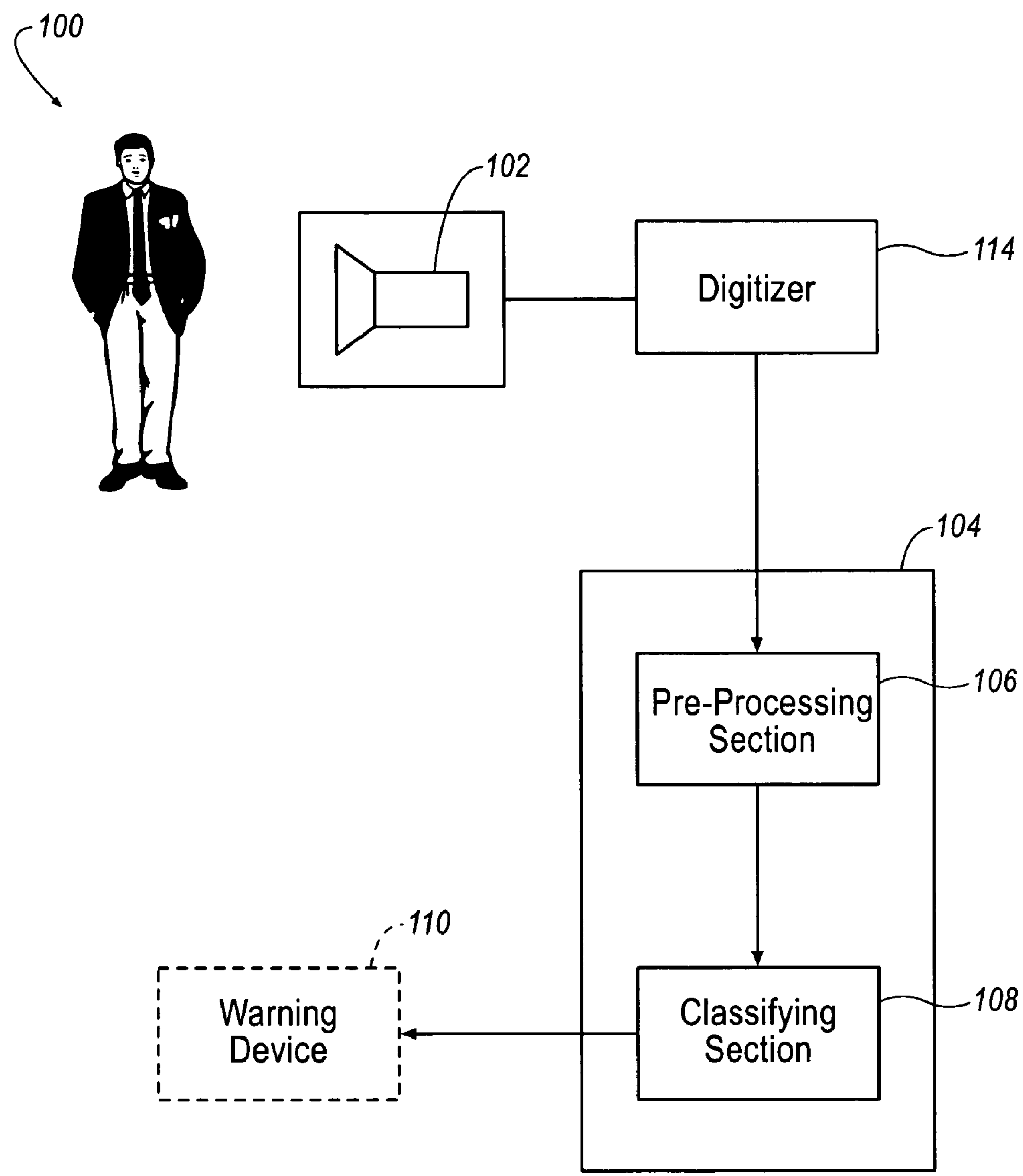
FIG. 2 is a block diagram showing an embodiment of the present invention.

With reference to FIG. 2, the image acquisition device 102 is connected to a visual awareness processor 104. The visual awareness processor 104 includes pre-processing section 106 and a classifying section 108. The visual awareness processor 104 may be further connected to a warning device 110 (shown in phantom in FIG. 2).

Referring back to FIG. 1, an infrared illuminator 112 directs infrared radiation (IR) toward a facial region of an operator wherein a camera 102 is situated to detect the radiation reflected therefrom to capture an image. The camera 102 may include a charge coupled device (CCD) to acquire an image. In this configuration, several light intensity values are captured by an array of photosites located across the CCD and electronically transferred to a digitizer 114. Then the digitizer 114 measures the various charges across the array of photosites to convert or represent the charge intensity into a digital format. In another embodiment, a high resolution complementary metal oxide semiconductor (CMOS) device may be implemented to achieve substantially equivalent results as the CCD. Next the digital information is sent to the visual awareness processor 104 for analysis.

Figure 3:
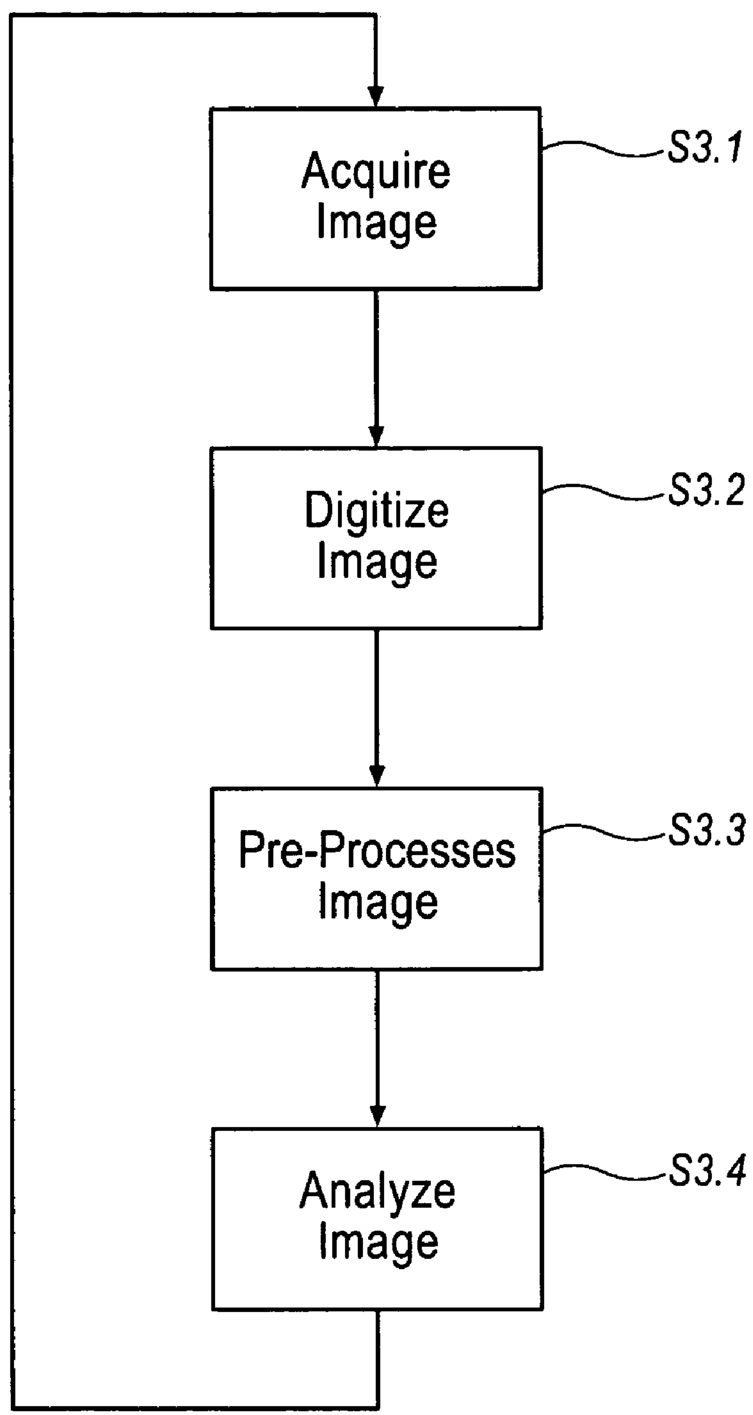
FIG. 3 is a flowchart showing a method to determine driver awareness according to an embodiment of the present invention.

The visual awareness processor 104 includes, for example, a CPU (Central Processing Unit) that implements each process to be described. With reference to FIG. 3, a flowchart is shown and generally describes a method for determining visual awareness according to an embodiment of the present invention. The visual awareness system 100 acquires or captures an image of an object in step S3.1, digitizes the image in step S3.2 to create a digital signal representation of the image, pre-processes the image in step S3.3 as described herein, then analyzes the object in the image to gauge or measure the likelihood of visual distraction in step S3.4. Steps 3.1 through 3.4 are then repeated to measure later instances of visual distraction while the visual awareness system 100 is in operation.

The image information is passed from the digitizer 114 to the visual awareness processor 104 by way of digital signal to a pre-processor 106 in Step 3.3. Step 3.3 is described in more detail in FIG. 4. First, the image pre-processor 106 identifies a particular region of the image of the object captured within the image in step S4.1. Defining the focus upon a particular region limits the processing time to that particular region and also limits system errors that occur due to physical differences in and around the facial region. Such variations include, but are not limited to, changes in operator height, head orientation, head shape, facial hair, seat position, camera position, or the like.

The particular region may be either manually specified or dynamically determined by algorithms known to the system. Such algorithms are referred to generally, as they are the subject of prior art, and, thus, will be readily apparent to one of skill in the art.

One of such dynamic systems determines the particular region by first referencing a distinguishing feature. The distinguishing feature may include without limitation; eyes, ears, the corners of the mouth, or the like. For purposes of convenience, one embodiment of the invention will use the eyes as the distinguishing feature, however, it should be noted the invention may be similarly practiced using any desirable distinguishing feature. With continued reference to FIG. 4, a first eye is identified and tracked by the image pre-processor 106 within the captured image in step S4.1. Such identification and tracking techniques are common and, therefore, will generally be known in the art. Since, generally, the maximum distance between eyes will not exceed a particular amount, a distance $d_{max}$ may additionally be applied to constrain or direct the pre-processor where to generally search for a second eye in step S4.2 Thereupon, a second eye is located in step S4.3. Upon locating the second eye, the particular region may be statically sized therearound, or, alternatively, dynamically sized relative to a horizontal distance between the eyes $d_{eye}$ in step S4.4. The particular region is sized to at least include the first and second eyes and the nose. However, the particular region may also include the nose, or additionally include the ears or mouth.

Distinguishing features such as the eyes are utilized because the region substantially therearound maintains a generally stable light environment, whereas other facial regions yield larger light fluctuations. Moreover, eye luminosity remains relatively constant in substantially every lighting environment. That is, the eye luminosity remains relatively unaffected whether the analysis is performed during the day or night. Even moreover, the eyes remain relatively fixed and are generally unaffected by operator facial variations resultant from activities including, but not limited to, eating, drinking, talking, or the like. Such conditions are typically referred to as face occlusions. During these instances, many facial features appear different and thereby yield less accurate results.

Once the distinguishing feature is identified and the particular region becomes sized and established, the particular region is next augmented and normalized using image distribution enhancement techniques. Such augmentation or enhancement techniques help to address image distortions that may adversely affect analysis of the particular region. Examples of these and other distortions include variations in lighting, skin-tone, skin reflectivity, head depth, head rotation, or the like. Such variations result in significant fluctuations in the intensity distribution, the contrast, and the like of the tracked features. Moreover, the augmentation is intended to at least highlight or enhance the facial disparities that are particularly noticed during operator movement, and thereby provide a clearer image in terms of the present analysis to improve the accuracy of the results.

The particular region is transformed using at least one of a linear intensity affine transformation and a histogram equalization. That is, first a linear intensity affine transformation is applied over each pixel within the particular region in step S4.5 to reduce the amount of shadows by increasing their brightness levels, yet leave the pupil, iris and nostrils substantially identifiable, since the intensity values of shadows are usually larger than the receptive fields of the pupil, iris and nostrils. In an embodiment, more specifically, the linear intensity transformation is described as $I(i)=a \times I(i)+b$, where $I(i)$ is the $i^{th}$ pixel in the image, and a and b are the affine factors. In an embodiment a=1.7 and b=0. A histogram equalization is applied to the particular region in step S4.6 to darken the pertinent facial features, such as the nose and the eyes, and brighten the skin.

Figure 4:
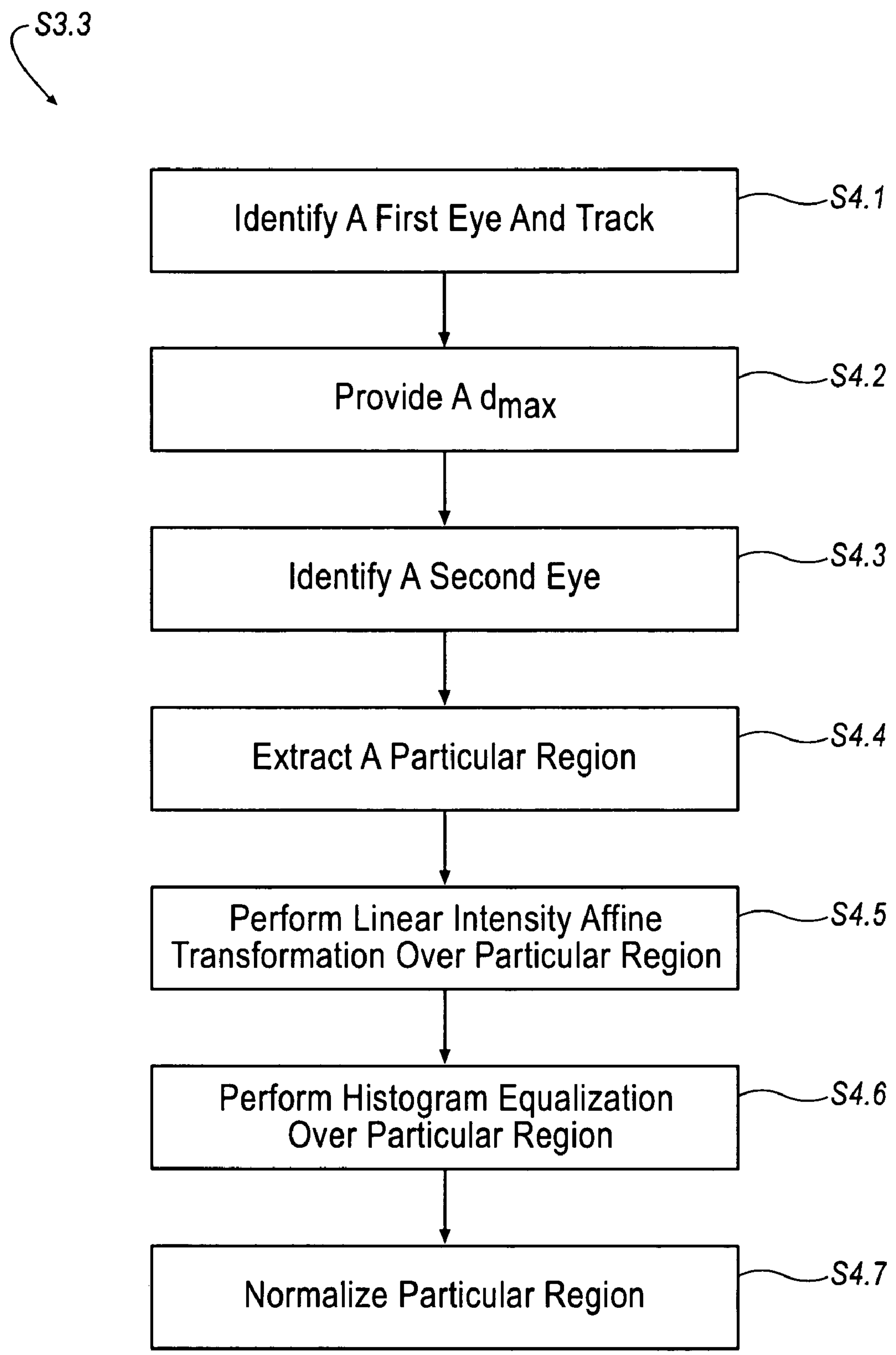
FIG. 4 is a flowchart showing a method to determine, enhance and normalize a particular region according to an embodiment of the present invention.

With further reference to FIG. 4, the size of the particular region is normalized to a fixed, or predefined size in step S4.7. In an embodiment, since the particular region is dynamically determined with respect to $d_{eye}$ the size of the particular region varies from operator to operator and should be standardized. Various techniques may be employed to normalize the particular region and one of skill in the art will recognize the advantages of such. Thus, among other possibilities, a next neighbor down sample may be used.

With reference to FIG. 3 and FIG. 4, the enhanced and normalized particular region is next communicated to the analysis section 108 for image analysis in step S3.4. A method for analyzing the image as shown in Step 3.4 is shown and described in FIG. 5. In an embodiment, the analysis is done using eigen methods because face images have substantially similar structures which may be vectorally represented in a lower dimensional subspace without losing a significant amount of detail.

A method for using eigen theory to detect the facial position, and therefore, the driver awareness is described. Eigen theory is but one mathematical technique to vectorally relate images. Therefore, other image vector relating techniques may similarly be implemented which will become recognizable to one of ordinary skill in the art when combined with the present disclosure. Thus for example, support vector machines may carry out the invention as described.

Figure 5:
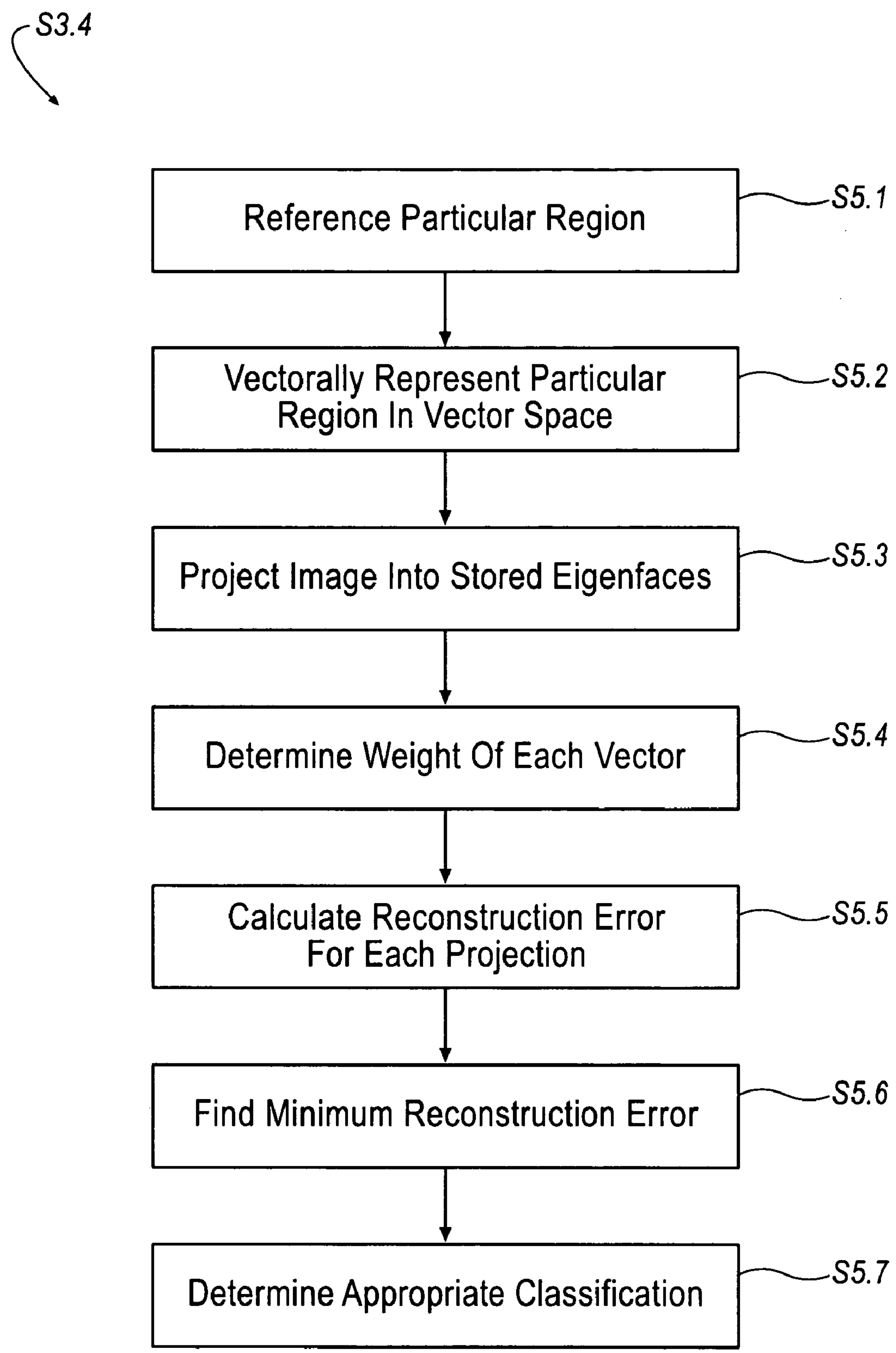
FIG. 5 is a flowchart showing a method to classify driver position according to an embodiment of the present invention.

With reference to FIG. 5, the particular region is referenced as a face image in step S5.1. The image is then vectorally represented as a point in a high dimensional vector space in step S5.2. Specifically the 2D image matrix is converted to a 1D raw vector using well known matrix linearization transformation techniques. The image is next projected into at least one stored or pre-trained prototype of a face image in an eigenspace in step S5.3 (also known as an 'eigenface'). Once the image is projected into the eigenspace, a weight of each vector is determined by a corresponding set of weights pertaining to eigenvectors in the eigenface S5.4.

An eigenface is a set of eigenvectors derived from the covariance matrix of the probability distribution of the high dimensional vector space of possible faces. To generate the eigenface a set of representative images are normalized as described in the normalization step for the particular region in step S4.7. They are sampled at the pixel level (m×n) and treated as mn-dimensional vectors whose components are the values of their pixels. The eigenvectors of the statistical distribution of the face image vectors are then extracted. The eigenvectors are weighted to determine which vectors create the identifiable facial characteristics. The shorter eigenvectors are given lesser weight and, in an embodiment, are cast out as noise. The longer eigenvectors are more pertinent to the classification step as they are given greater weight and describe distinguishing facial features.

A predefined eigenface is provided that represents various driver orientations. In the current example, three eigenfaces are predefined. The predefined eigenfaces represent left, frontal, and right operator orientations. With continued reference to FIG. 5, once the image is projected into each of the eigenspaces in step S5.3, a measurement is calculated for each eigenspace ($d_{left}$, $d_{frontal}$, $d_{right}$) that provides an average distance between the projected vectors and their corresponding eigenvectors in step S5.5. This distance is known as a reconstruction error.

Figure 6:
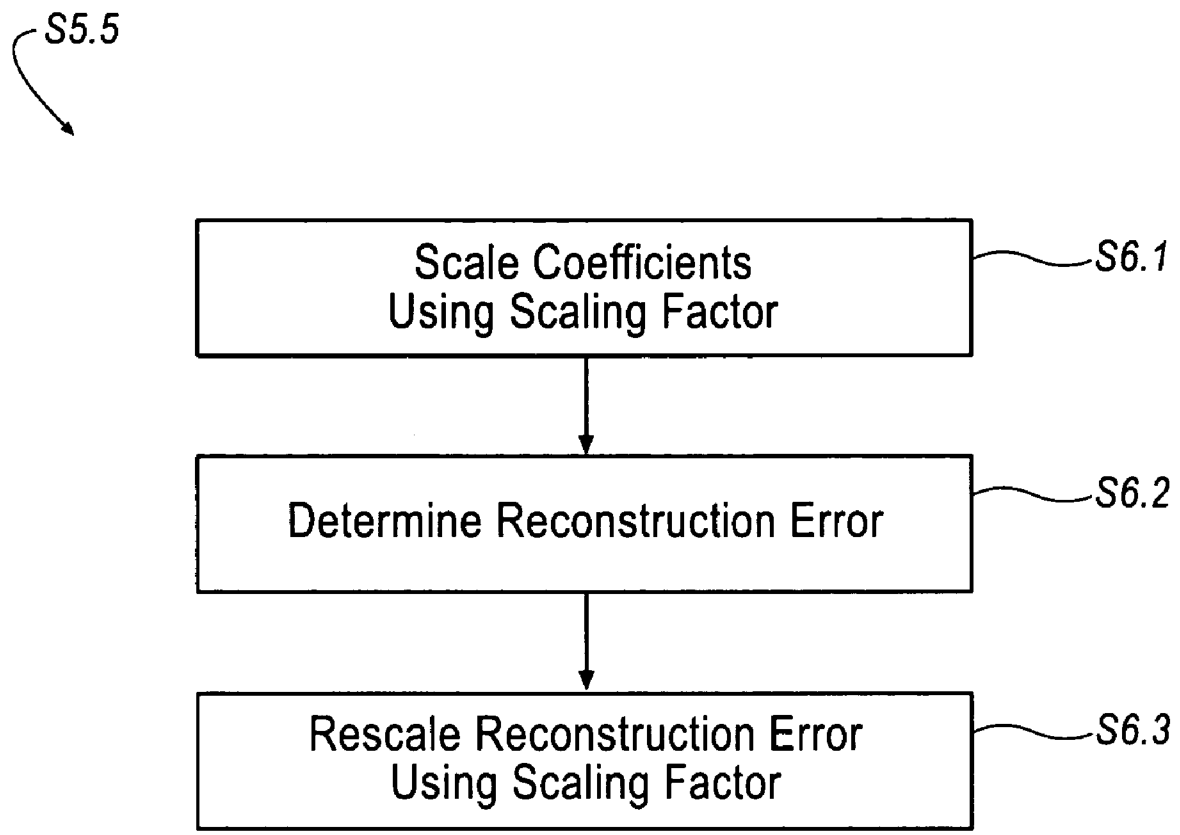
FIG. 6 is a flowchart showing a method to determine a reconstruction error according to an embodiment of the present invention.

An embodiment to calculate this reconstruction error as provided in step S5.5 of FIG. 5 is shown in FIG. 6. Let x represent the input vector of the face pose; U represent the matrix of the eigen vectors of the image space; AVE represent the average vector of the class; r represent the reconstruction stage; e represent the reconstruction error; and y represent the sum of products, namely $y=U'(x-AVE)$. With reference to FIG. 6 the coefficients are scaled to integer values between −128 and 127 so that they may be represented and calculated using only 8-bits and fixed point operations in step S6.1. The scaling factor may be preset within the system or dynamically determined by the system. The reconstruction error is then determined in step S6.2. In an embodiment, then, $r=AVE+Uy$; and $e=\Sigma|x_i-r_i|$. The reconstruction error is then scaled back to the original range and domain using the inverse of the stored scaling factor in step S6.3. The process is then repeated until a reconstruction error is determined for each predefined eigenface and input vector.

Referring now back to FIG. 5, the reconstruction errors are next compared to one another to find the eigenface and input vector relationship with the lowest reconstruction error in step S5.6. The image is then given the appropriate classification in step S5.7.

Although the reconstruction is described using fixed point techniques, as speeds of processors increase and other technologies advance it may become insignificant whether fixed point or floating point values are used. Moreover, although one method using eigen theory is disclosed, other methods employing eigen theory may be equally employed to determine facial position. Such methods will become readily apparent to one of ordinary skill in the art in combination with this disclosure.

The orientations of the predefined eigenface positions are determined according to the field of view of the operator. For illustrative purposes, the term 'frontal position' is used in this disclosure to refer to an operator that is not distracted, and the eigenface for the frontal position represents the baseline or the 0-degree operator reference position (i.e. the operator is directly faced forward). Extensive research has shown that a 9 degree to a 14 degree facial position deviation from the baseline in either direction (distracted left or distracted right) typically marks a boundary that indicates a distracted operator. In other words, when an operator is in the frontal position, their facial position is substantially confined between ±(9 to 14) degrees. More specifically, their facial position is between ±(10 to 13) degrees. Conversely, as operators turn their attention away from the forward road, their facial position approaches and crosses this boundary. The boundary values, therefore, are generally an accurate determination of visual awareness, and indicate that facial position may be used to determine overall levels of visual awareness. This and other advantages will be apparent to those of ordinary skill in the art having reference to the specification in conjunction with the drawings.

Referring back to FIG. 2, the visual awareness system 100 may then be connected to a warning device as illustrated in phantom at 110. In an embodiment once an image of the operator is classified as left or right a warning device is triggered. In an embodiment as illustrated at FIG. 7 and FIG. 8, once the system classifies the operator facial position the system next determines whether a warning is appropriate due to driver distraction over a period of time.

Figure 7:
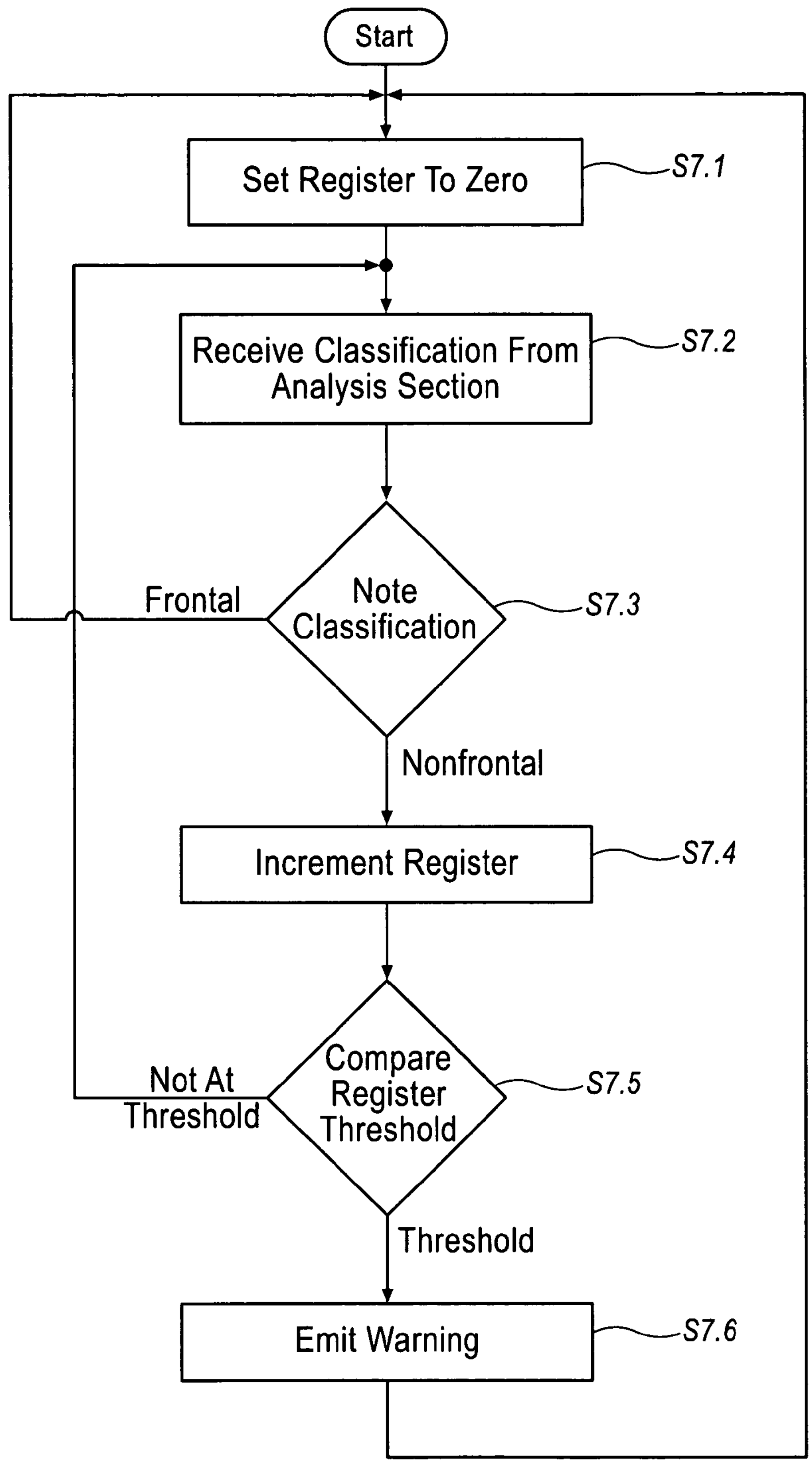
FIG. 7 is a flowchart showing a method to determine driver awareness according to an embodiment of the present invention.

With reference to FIG. 7, a register is provided and is initially set to zero in step S7.1. Next in step 7.2, the warning device 110 receives an image classification determined by said visual awareness processor 104. The classification is then evaluated in step S7.3. More specifically, if the operator is classified in the frontal position, then the visual awareness system 100 simply repeats the analysis and classification step as provided in FIG. 5, and the process returns to step S7.1. Otherwise, if the image is classified as non-frontal, the register records or is incremented to reflect a distracted operator S7.4. Thereupon, the system determines whether the register has reached a pre-defined threshold in step S7.5. If the register reaches the predefined threshold, a sensory warning is generated in S7.5. Otherwise the system returns to S7.2. In an embodiment, the warning device 110 resets the register each time the operator returns to the frontal position. Current research indicates that as the peak non-frontal duration approaches 2 seconds, the probability of visual distraction is high. If this occurs, a sensory warning may be emitted by the warning device 110 to remind the operator of their primary task, that is, the safe passage of the vehicle and its contents. The type of sensory warning may be based on a number of factors including cost efficiency, operator preference, or the like.

Figure 8:
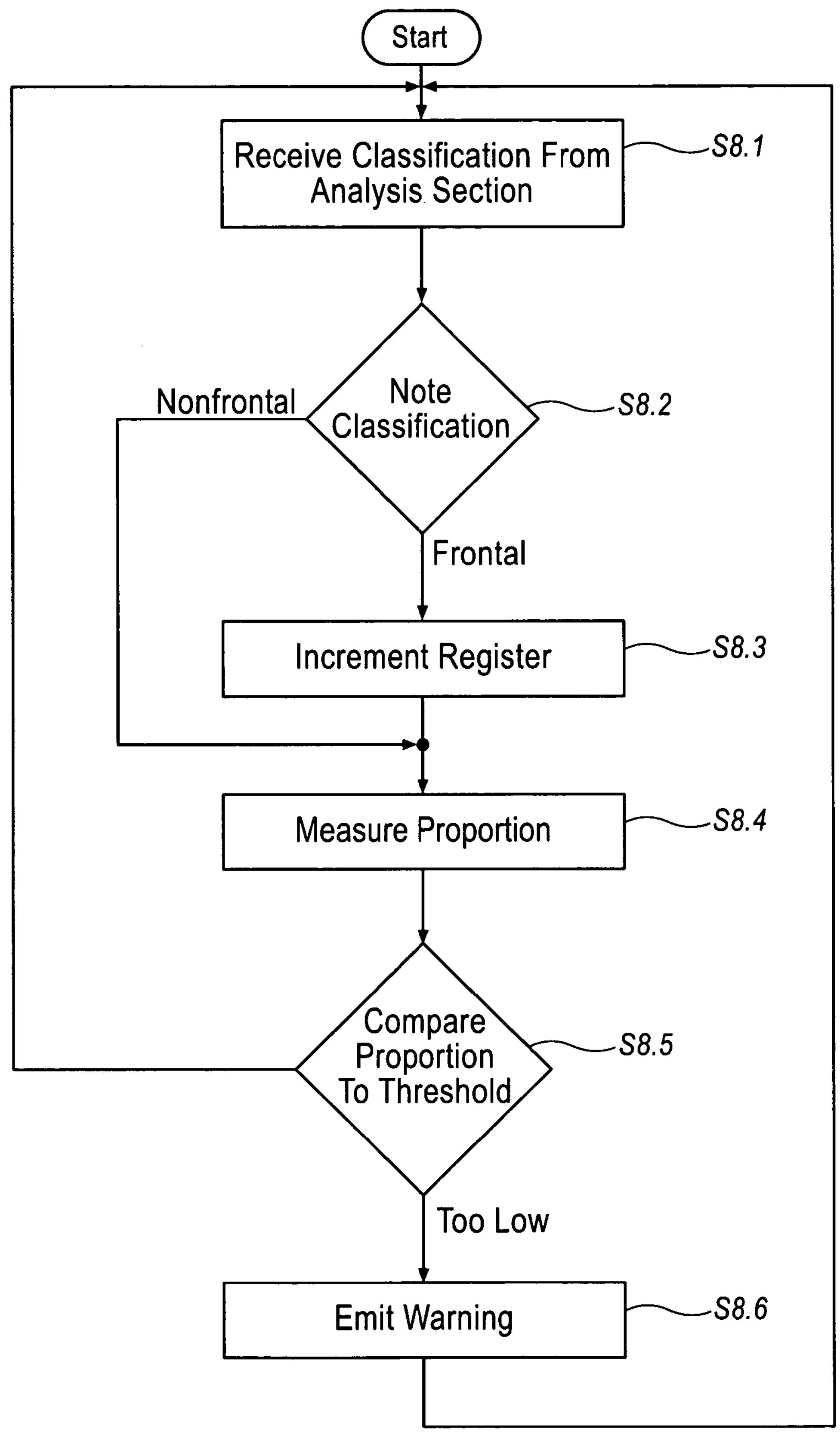
FIG. 8 is a flowchart showing a method to determine driver awareness according to an embodiment of the present invention.

In another embodiment, as illustrated in FIG. 8, the visual awareness system 100 determines driver awareness by measuring the proportion of time that the visual awareness processor 104 classifies the operator in the frontal position. One way to achieve this, for example, employs a binary scheme. In an embodiment, the warning device 114 receives the operator classification from the analysis section in step S8.1. The warning device 114 notes the classification in step S8.2. If the facial position is classified as being in the frontal position, a register is incremented to record the classification of the position S8.3. Similarly, if the operator image is classified as non-frontal, namely distracted left and distracted right, the register is not incremented and skips step S8.3. Thereafter, a proportion of the register value is measured in step S8.4. If the proportion is higher than a pre-defined threshold, then there is a high probability that the operator is likely not distracted in step S8.5. If the proportion is lower or equal to the pre-defined threshold, then the operator is likely distracted as indicated in step S8.6. At this point, a sensory warning may be provided in step S8.6. In an embodiment, a five second time window is used in a 30 Hz system, which provides that the facial position will be classified a total of 150 times. In an embodiment, the pre-defined threshold is between 0.45 and 0.6. However, the threshold may be adjusted according to the preferences or quality of the operator.

While the foregoing has described what are considered to be preferred embodiments of the present invention, it is understood that various modifications may be made therein and that the invention may be implemented in various forms and embodiments, and that it may be applied in numerous applications, only some of which have been described herein. It is intended by the following claims to claim all such modifications and variations which fall within the true scope of the invention.

What is claimed is:

1. An awareness detection system, comprising:

an imaging device adapted to acquire data representative of an image of a subject; and an awareness processor connected to said imaging device, wherein said awareness processor is adapted to determine a particular region within said image, size and establish said particular region, augment and normalize data of said image in said particular region with a distribution enhancement technique, represent said image within a fixed space with a vector relating technique that includes a reconstruction error determined in a fixed point system relative to a floating point system, which is used to classify an awareness state of the subject according to an orientation of the subject represented by the normalized data and said vector relating technique.

2. The system according to claim 1, wherein said classification is determined according to a facial orientation of the subject.

3. The system according to claim 2, wherein said awareness processor includes a pre-processing logic module that is adapted to identify a first eye and a second eye of the subject and a distance therebetween, and wherein said pre-processing logic module is adapted to generate said particular region according to said distance.

4. The system according to claim 1, further comprising a warning device connected to said awareness system that generates a sensory warning when said awareness processor classifies the subject state as distracted.

5. The system according to claim 1, wherein said awareness processor includes a pre-processing logic module that enhances said particular region with said distribution enhancement technique, which includes performing a linear intensity affine transformation firstly, and a histogram equalization secondly.

6. The system according to claim 1, wherein said awareness processor includes a classifying logic module that is adapted to vectorally project the particular region into at least two eigenfaces, wherein each projection includes said reconstruction error, and wherein said classifying logic module is adapted to classify said particular region according to a minimum reconstruction error.

7. The system according to claim 6, further comprising three eigenfaces, one of said eigenfaces representing the subject in an undistracted state, the other two of said eigenfaces representing the subject in a distracted right position and distracted left position.

8. The system according to claim 7, wherein said other two of said eigenfaces are arranged approximately greater than +/−9 degrees from said undistracted eigenface.

9. The system according to claim 6 further comprising, a warning device connected to the classifying logic module that generates a sensory warning when the subject is distracted for a predefined period of time.

10. The system according to claim 9, wherein said predefined period of time is at or about 2 seconds.

11. The system according to claim 1, wherein said imaging device is a single imaging device, such that said awareness processor classifies such awareness state based upon said image received from said single imaging device.

12. The system according to claim 1, wherein coefficients of said vector relating technique are scaled to an integer value between −128 and 127, such that said coefficients are represented and calculated using 8-bits and said fixed point system.

13. A method for determining awareness of a subject, comprising the steps of:

acquiring data representative of an image of a subject, wherein said image is acquired by an imaging device;

processing said data by an awareness processor, said processing including, identifying a particular region of said image data; and augmenting and normalizing the data in said particular region to a pre-defined size with a distribution enhancement technique;

representing said image within a fixed space with a vector relating technique that includes a reconstruction error determined in a fixed point system relative to a floating point system; and classifying subject awareness based on the orientation of a portion of the subject represented by the normalized data in said particular region and said vector relating technique.

14. The method according to claim 13, wherein the step of augmenting and normalizing comprises the steps of:

performing a linear intensity affine transformation on said data in said particular region; and performing a histogram equalization on said data in said particular region.

15. The method according to claim 14, wherein said performing a linear intensity affine transformation step is performed before said performing a histogram equalization step.

16. The method according to claim 13, wherein said identifying a particular region step further comprises the steps of:

identifying a first eye of the subject;

identifying a second eye of the subject;

calculating a distance between said first and second eyes of said subject; and sizing said data in said particular region according to said distance between said first and second eyes of the subject.

17. The method according to claim 13, wherein said system is adapted to store a frontal eigenface that represents an undistracted subject and is referenced at 0 degrees, a right eigenface that represents a distracted subject facing right, and a left eigenface that represents a distracted subject facing left, and said processing said data step further includes, representing said particular region vectorally;

projecting said particular region into each of said eigenfaces;

calculating said reconstruction error for each of said projections;

determining the minimum reconstruction error; and classifying said subject as frontal or non-frontal according to said determining step.

18. The method according to claim 17, wherein said stored right and left eigenfaces are approximately greater than +/−9 degrees from said frontal eigenface.

19. The method according to claim 13 further comprising the step of:

producing a warning when the subject is distracted for a predetermined period of time.

20. The method according to claim 19 wherein said predetermined time is at or around two seconds.

21. The method according to claim 13, wherein coefficients of said vector relating technique are scaled to an integer value between −128 and 127, such that said coefficients are represented and calculated using 8-bits and said fixed point system.

* * * * *